(12) United States Patent
Robinson et al.

(10) Patent No.: US 9,057,639 B2
(45) Date of Patent: Jun. 16, 2015

(54) REDUCED GRAPHENE OXIDE FILM

(75) Inventors: Jeremy T. Robinson, Washington, DC (US); Eric S Snow, Springfield, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/455,563

(22) Filed: Apr. 25, 2012

(65) Prior Publication Data
US 2012/0208027 A1  Aug. 16, 2012

Related U.S. Application Data (62) Division of application No. 12/366,833, filed on Feb. 6, 2009, now Pat. No. 8,182,917.

(60) Provisional application No. 61/038,137, filed on Mar. 20, 2008.

(51) Int. Cl.
| | | |
|---|---|---|
| B05D 3/12 | (2006.01) |
| G01G 3/16 | (2006.01) |
| B82Y 20/00 | (2011.01) |
| B82Y 30/00 | (2011.01) |
| G01N 5/00 | (2006.01) |
| H01H 1/00 | (2006.01) |
| B05D 1/00 | (2006.01) |
| B32B 37/24 | (2006.01) |
| H01H 59/00 | (2006.01) |

(52) U.S. Cl.
CPC ........... *G01G 3/16* (2013.01); *Y10T 428/24562* (2015.01); *Y10T 428/30* (2015.01); *B05D 1/005* (2013.01); *B32B 2037/243* (2013.01); *B32B 2309/105* (2013.01); *B82Y 20/00* (2013.01); *B82Y 30/00* (2013.01); *G01N 5/00* (2013.01); *H01H 1/0036* (2013.01); *H01H 59/0009* (2013.01); *H01H 2203/012* (2013.01)

(58) Field of Classification Search
CPC ........ B05D 1/005; B82Y 20/00; B82Y 30/00; B32B 2037/243
USPC ......................................... 427/240, 425, 377
See application file for complete search history.

(56) References Cited

U.S. PATENT DOCUMENTS

| | | | |
|---|---|---|---|
| 6,777,350 B2 * | 8/2004 | Nakagawa | 438/782 |
| 7,914,844 B2 * | 3/2011 | Stankovich et al. | 427/58 |
| 8,329,762 B2 * | 12/2012 | Chane-Ching et al. | 516/78 |
| 2008/0048152 A1 * | 2/2008 | Jang et al. | 252/378 R |
| 2008/0248275 A1 * | 10/2008 | Jang et al. | 428/220 |
| 2010/0144904 A1 * | 6/2010 | Wang et al. | 516/98 |

OTHER PUBLICATIONS

Gilje et al. "A Chemical Route to Graphene for device Applications," Nano Letters, vol. 7, No. 11, pub. Oct. 2007, pp. 3394-3398.*
Becerril et al., "Evaluation of Solution-Processed Reduced Graphene Oxide Films as Transparent Conductors," Feb. 9, 2008, ACS Nano, vol. 2, No. 3, pp. 463-470.*

* cited by examiner

*Primary Examiner* — Kirsten Jolley
(74) *Attorney, Agent, or Firm* — US Naval Research Laboratory; Joseph T. Grunkemeyer

(57) ABSTRACT

Spin coating a mixture of graphene oxide platelets, water, and an organic solvent by placing a drop of the mixture on a spinning substrate while blowing a drying gas onto the substrate and allowing the water and the organic solvent on the substrate to evaporate; and repeating the spin coating one or more times to form a graphene oxide film in contact with the substrate. An about 1-100 nm thick film of overlapping platelets of reduced graphene oxide.

20 Claims, 10 Drawing Sheets

REDUCED GRAPHENE OXIDE FILM

The application is a divisional application of U.S. patent application Ser. No. 12/366,833, allowed and filed on Feb. 6, 2009, which claims the benefit of U.S. Provisional Patent Application No. 61/038,137, filed Mar. 20, 2008. This provisional application and all other publications and patent documents referenced throughout this nonprovisional application are incorporated herein by reference.

TECHNICAL FIELD

The invention is generally related to thin films of reduced graphene oxide.

DESCRIPTION OF RELATED ART

Molecular detection using fullerene nanomaterials (i.e., $sp^2$-bonded carbon structures of single atomic layer thickness) is a promising area of nanotechnology. Fullerenes are relatively inexpensive, thermally and chemically stable, come in a variety of different geometries (spheres, tubes, and sheets), can be grown and processed with high precision, and are generally process-compatible with conventional microlithographic techniques. Moreover, because every atom in a fullerene is a surface atom, electron transport through these materials can be highly sensitive to adsorbed molecules. This phenomenon has subsequently enabled the fabrication of sorption-based sensors capable of detecting trace levels of vapor using conventional low-power electronics.

Previous efforts are built upon single-walled carbon nanotubes (SWNTs), where the sensing transduction mechanism is based upon changes in conductance due to charge transfer or mobility change (Collins et al., *Science*, 287(5459), 1801-1804 (2000); Kong et al., *Science*, 287(5453), 622-625 (2000)) or capacitance from intrinsic or induced dipole moments (Snow et al., *Science*, 307(5717), 1942-1945 (2005)) when a molecular species interacts with the SWNT sidewalls. Though exact details of the interaction chemistry remain elusive, it is clear that molecular interactions with defect sites in SWNT sidewalls can dominate their electrical response, (Robinson et al., *Nano Lett.*, 6(8), 1747-1751 (2006)) that the interactions of a molecule with a $sp^2$-bonded carbon site differ dramatically from those with a high-energy defect site, and that controlling the defect density can enhance sensor sensitivity and specificity (Robinson et al.). However, the optimal defect density will balance the gains in sensitivity against the rapid degradation in conductivity due to the defects. Only recently has nanometer-thick suspended sheets of graphene with lateral dimensions of only a few microns been achieved (Bunch et al., "Electromechanical Resonators from Graphene Sheets" *Science*, 315, 490 (2007)).

BRIEF SUMMARY

Disclosed herein is a method comprising: providing a mixture of graphene oxide platelets, water, and an organic solvent; spin coating the mixture by placing a drop of the mixture on a spinning substrate while blowing a drying gas onto the substrate and allowing the water and the organic solvent on the substrate to evaporate; and repeating the spin coating one or more times to form a graphene oxide film in contact with the substrate.

Also disclosed herein is a film comprising overlapping platelets of reduced graphene oxide. The film is from about 1 nm to about 100 nm thick.

BRIEF DESCRIPTION OF THE DRAWINGS

A more complete appreciation of the invention will be readily obtained by reference to the following Description of the Example Embodiments and the accompanying drawings.

Note the large decrease in noise for the graphene oxide sensor, demonstrated by the "smoothness" of the curve, while maintaining the same sensitivity as the CNT sensor.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Described herein is an inexpensive method to produce large-area nanometer-thick films of electrically conducting reduced graphene oxide. Such films are compatible with conventional microprocessing techniques and have potential application as the active material for the direct electronic detection of chemical/biological analytes and as an electronic material for flexible large-area displays. It is further disclosed that these nanometer-thick films can be selectively removed from the substrate and transferred in-tack to other surfaces. If the transfer is made to a textured surface, the films can form suspended membranes with potential application in nanomechanical devices, electromechanical optical modulators, permeable membranes, filters for organic and biomolecular species, and nanofluidics.

Graphene oxide (GO) is an electrically insulating material composed of a single graphene sheet with oxygen functional groups bonded perpendicular to the graphene basal-plane (Lerf et al., "Structure of graphite oxide revisited" *J. Chem. B*, 102, 4477 (1998)). Due to oxygen functional groups such as carboxyls, epoxides, and alcohols, GO is hydrophilic and can readily exfoliate as single sheets when ultrasonicated in $H_2O$ (Stankovich et al., "Synthesis of graphene-based nanosheets via chemical reduction of exfoliated graphite oxide" *Carbon*, 45, 1558 (2007)). The average size of an individual GO sheet after oxidation and suspension in $H_2O$ may be 1 $\mu m^2$ or less, with a thickness of approximately 1 to 1.5 nm.

Graphene oxide can be reduced back to graphene by the removal of the oxygen function groups and recovery of the aromatic double-bonded carbon. Chemical reduction using hydrazine hydrate demonstrates that the conductivity of GO flakes can be increased by four- to five-orders of magnitude (Gilje et al., "A Chemical Route to Graphene for Device Applications" *Nano Lett.*, 7, 3394 (2007)). In addition, the mobility of reduced flakes exhibit field effect mobilities between 2 to 200 $cm^2/V \cdot s$ (Gomez-Navarro et al., "Electronic Transport Properties of Individually Chemically Reduced Graphene Oxide Sheets" *Nano Lett.*, 7, 3499 (2007)).

In addition to electronic/sensor applications, reduced GO has potential application in nanomechanical devices. Suspended nanostructures may be free from substrate interactions such as van der Waals forces, which makes them desirable for mechanical, electrical, and nanoelectromechanical applications.

A technique has been developed to produce nanometer-thick films of reduced graphene oxide that are continuous and a few monolayers thick. Briefly and by example, the process may begin by centrifuging already exfoliated GO platelets suspended in water. The resulting wet solids are isolated and resuspended in methanol or acetone. Though resuspended in nominally pure methanol the GO material does not agglomerate, which is attributed to the retention of a surfactant water layer on individual platelets (Titelman et al., "Characteristics and microstructure of aqueous colloidal dispersions of graphite oxide" *Carbon*, 43, 641-649 (2005)). From this solution GO films are deposited on $SiO_2$/Si substrates by a modified spin-casting method. Single droplets are released on the spinning substrate and nitrogen is immediately blown over the sample to accelerate evaporation with a controllable drying front. This process can result in continuous thin films that are locally uniform with GO platelets laying flat on the surface. Film thickness may be controllable on nanometer length scales by varying either the concentration of GO platelets in solution (typically 0.5 mg/mL to 3.0 mg/mL) or the volume of solution used during spin-casting.

Thickness variations across the sample can be minimized by adjusting the direction of nitrogen flow across the sample during spin-casting. Alternatively, the platelets can be deposited onto a surface using an airbrush, although the films exhibit a higher degree of local non-uniformity. After deposition GO films are reduced using a hydrazine hydrate vapor. This increases GO film conductivity between $10^4$ to $10^5$ times. Subsequent to reducing the GO film, samples are processed into electronic devices or sensors using standard photolithography.

The spin coating method may be performed using a mixture of graphene oxide platelets, water, and an organic solvent. The platelets may be made by methods known in the art, such as oxidation of graphite by the Hummers method (Hummers et al., "Preparation of graphitic oxide" *J. Am. Chem. Soc.*, 80, 1339 (1958)) followed by ultrasonication. Methanol and acetone may be suitable solvents, and the mixture may include as much as 80% or more methanol.

The drop of the mixture may be any volume or concentration and may be spin coated at any speed. A suitable drop size is from about 5 µL up to about 10 µL or about 100 µL. A suitable spinning speed is from about 2000 to about 6000 RPM. In general, the properties of the film may be improved by using smaller drops and faster speeds. By doing so, more repetitions of the spin coating are needed in order to produce a given film thickness.

A single spin coating from a single drop of the mixture may produce a sub-monolayer of GO platelets on the substrate. Repeating the spin coating on the same part of the same substrate can build up a thicker film of GO platelets. The spin coating may be repeated, for example, up to about 200-300 times. For example 5 µL drops may be spin coated 300 times. The final film may contain mostly platelets that are generally parallel to the substrate (meaning that they are closer to parallel than perpendicular), with most platelets overlapping more than one neighboring platelet.

Figure 2:
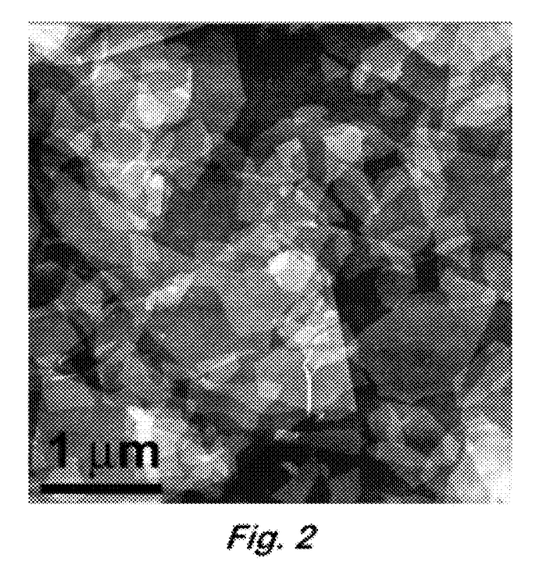
FIG. 2 shows an atomic force microscopy (AFM) image showing a graphene oxide thin-film on a 250 nm $Si/SiO_2$ substrate that was deposited via spin-coating.

The use of organic solvent, small drop size and simultaneous drying may produce an improved film morphology compared to the films of similar thickness made by a single spin coating of a large drop of an aqueous mixture. Films made without organic solvent and/or with a single spin coating (or other coating method) may contain relatively large wrinkles Films made by the presently disclosed methods may have a reduced number of such wrinkles, or be entirely free of the wrinkles FIG. 2 shows an atomic force microscope image of a few-monolayer sample film.

After forming the GO film, the GO platelets may be at least partially chemically reduced. This may be done, for example, by exposing the film to hydrazine hydrate or by annealing in an inert gas, hydrogen, or vacuum. The reducing of the film removes some, but not all, of the oxygen atoms to produce reduced graphene oxide (rGO) platelets. This can raise the conductivity of the film to as high as 1 S/cm or higher. Some oxygen atoms remain in the rGO film, which can improve structural integrity and sensing properties of the film. Oxygen functional groups can allow hydrogen bonding between sheets for increased mechanical strength, in addition to providing stronger binding to substrates such as $SiO_2$. The film may have a Young's modulus of at least about 100 GPa.

After reducing, the film may be released from the substrate and placed onto another substrate without damaging the film. Sodium hydroxide or potassium hydroxide solution may be used to release the film. A desired film shape may be made by exposing only that shape to the releasing solution. The film may have a variety of functions depending in part on the structure of the substrate onto which it is transferred. The film thickness can be used to tune the mechanical, electrical, and optical properties of suspended GO membranes. These functions may be present in films made by the presently disclosed spin coating method, as well as other methods that produce a film of about 1-100 nm thick with overlapping platelets of reduced graphene oxide.

By forming a thin film first chemical bonding is reestablished between platelets in a more controlled manner. When a droplet of basic solution is placed on the reduced GO film the unreduced carboxylic acid groups are electrostatically stabilized (Muller et al., "Processable aqueous dispersions of graphene nanosheets" *Nat. Nano.*, 3, 101-105 (2008)) and surface tension at the interface of the droplet delaminates the film. When subsequently dipped into water the delaminated film floats on the surface; regions of the film unexposed to the basic solution remain attached to the substrate. The substrate material may affect the release of the film. The above chemical treatment of a multilayer graphene film formed by desorption on a SiC substrate does not result in film delamination, which may indicate that remnant oxygen functional groups play a role in this process.

The GO thin-film can alternatively be prepared for release from the substrate by thermal annealing. This can be either in place of the hydrazine hydrate reduction step or in combination with the hydrazine reduction step. Mechanical stability of the film can be tuned via thermal annealing.

The controlled deposition, delamination, and transfer of large area, reduced graphene oxide thin films opens the door to a variety of mechanical (Frank et al., "Mechanical Properties of Suspended Graphene Sheets" *J. Vac. Sci. Technol. B*, 256, 2558-2561 (2007); Poot et al., "Nanomechanical properties of few-layer graphene membranes" *Appl. Phys. Lett.*, 92, 063111-3 (2008)) and electromechanical experiments (Titelman et al. "Characteristics and microstructure of aqueous colloidal dispersions of graphite oxide" *Carbon*, 43, 641-649 (2005)). Despite the stresses introduced during the drying process, the films can remain in-tact with little observable damage. Films transferred onto pillars may have the highest probability of successful suspension since water can readily escape beneath the film. Depending on film thickness, films can be reproducibly suspended over hundreds of microns for a given pillar spacing. When transferred to a surface with holes the surface tension of the escaping water may draw the film inward, which remains whole and is most often partially suspended. Thicker films (>~10 nm) are more likely to remain intact.

The reduced GO films can show interesting mechanical properties. In all cases examined, films were suspendable over gaps larger than the lateral dimensions of single GO platelets. The thinnest suspended films have approximately the same thickness as a unit ordered stack observed in graphene oxide paper (Dikin et al., "Preparation and characterization of graphene oxide paper" *Nature*, 448, 457-460 (2007)).

The film may be placed on a substrate such that the film is in electrical contact with two electrodes on the substrate. Optionally, an electrical meter is in contact with the electrodes and an intake is used to contact a fluid sample, such as ambient air, to the film. The electrodes may be interdigitated. In this arrangement the film may be the active electronic material in chemical or biological sensors. The sensitivity and noise performance of reduced GO thin-film sensors depend on film thickness which can be optimized for different applications. The reduced GO thin-films may also be chemically modified to tailor their preformance as chemical or biological sensors.

Figure 10:
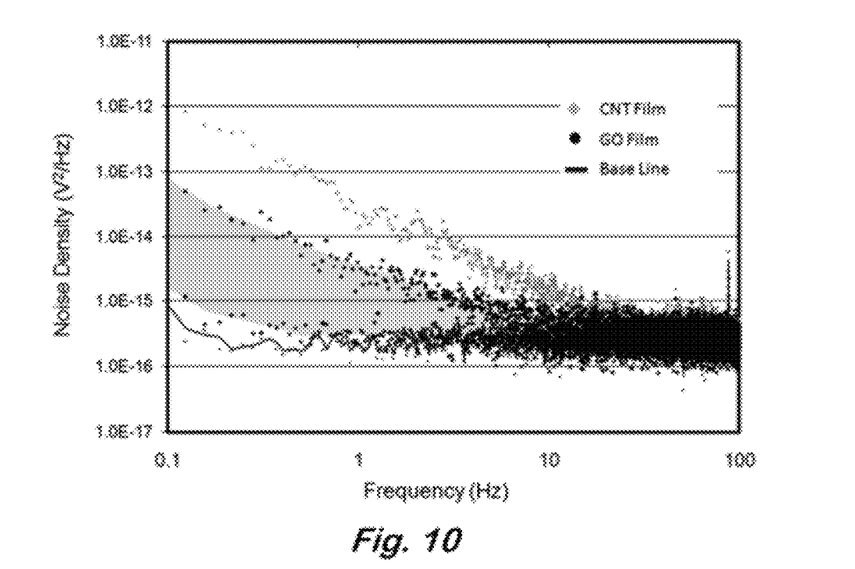
FIG. 10 shows a comparison of conductance noise response between a carbon nanotube sensor fabricated by Nanomix, Inc. (upper curve) and reduced graphene oxide sensors (middle curve). The noise level of graphene oxide films is tunable by varying the initial film thickness, which is demonstrated by the shaded region. Note the one- to two-orders of magnitude decrease in noise at low frequencies.
Figure 11:
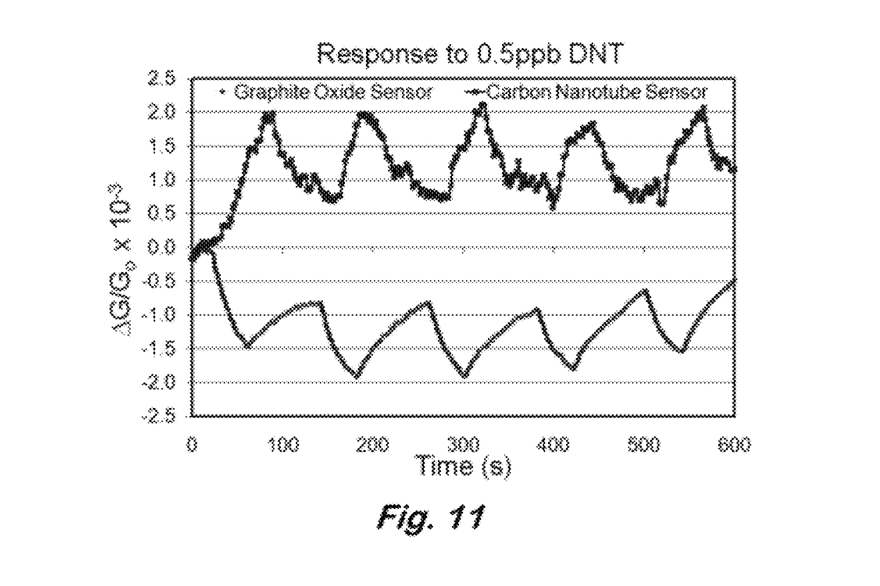
FIG. 11 shows conductance response to five pulses of DNT (an explosive simulant) of a carbon nanotube sensor fabricated by Nanomix, Inc. and a reduced GO thin-film sensor.

A reduced graphene oxide thin-film sensor may outperform carbon nanotube sensors. The sensor may operate by detecting the change in electrical properties caused by molecules adsorbed on the film surface, similar to carbon nanotube-based sensors (Snow et al., "Chemical vapor detection using single-walled carbon nanotubes" *Chem. Soc. Rev.*, 35, 790 (2006)). Unlike carbon nanotube-based sensors, which suffer from high levels of low-frequency noise due to their one-dimensional structure (Snow et al., "1/f Noise in Single-Walled Carbon Nanotube Devices" *Appl. Phys. Lett.*, 85, 4172 (2004)), reduced GO sensors are based on two-dimensional platelets and demonstrate superior noise sensitivity. A decrease in low-frequency noise of one- to two-orders of magnitude is possible (FIG. 10). Trace level detection of the explosives simulant DNT (dinitrotoluene) at 0.5 parts-per-billion with a response time of a few seconds has been demonstrated (FIG. 11).

The reduced GO thin-film chemical sensors may exhibit the following advantages over carbon nanotube-based sensors.

1) Increased signal: For a range of chemical analytes the conductance response of the graphene oxide sensor may be greater than pure carbon nanotube films.
2) Decreased noise: The two-dimensional natural of the reduced GO thin-film may allow for fewer charge fluctuations, resulting in a decrease in low-frequency noise of one- to two-orders of magnitude.
3) Versatile substrates: Reduced GO thin-films may be deposited at room temperature by spin-coating or air-brushing allowing the use of inexpensive flexible substrates.
4) Increased functionality: Graphene oxide can have considerably more oxygen functional groups than carbon nanotubes. It is expected that GO thin-films may be more readily functionalized, leading to chemical detection specificity.

In another embodiment a reduced GO thin-film is used as a transparent electrode or thin-film transistor. The GO thin-film may be almost completely transparent, as observed by a very slight color contrast between the film and substrate. After reduction, GO increases in conductivity by four- to five-orders of magnitude and can be modulated by 200-300%.

Figure 1:
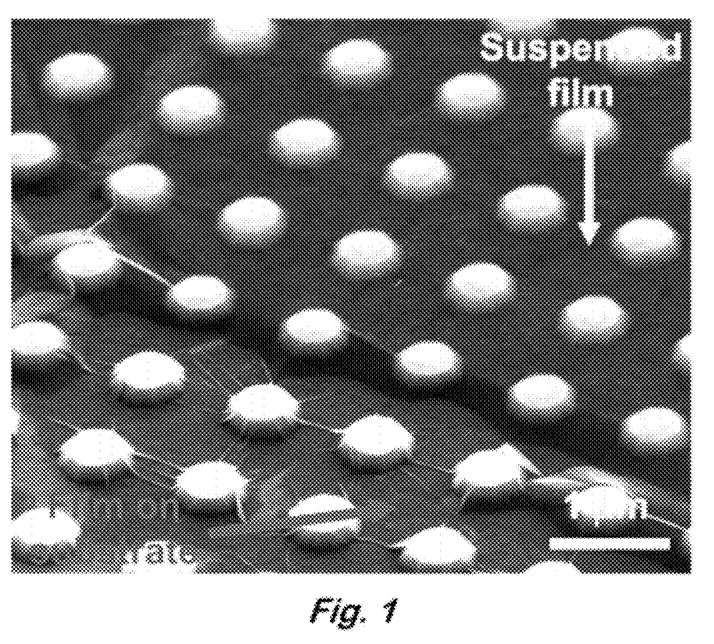
FIG. 1 shows a scanning electron microscope (SEM) image showing a 5 nm thick reduced GO film that was transferred to a substrate containing Si pillars (pillar height=130 nm, spacing=1 μm). The boundary between the suspended (upper right) and non-suspended (lower left) film is evident. Note the unsuspended film wraps closely over the Si pillars and forms wrinkles on the surface.

When subsequently re-captured on a textured or contoured substrate, portions of the reduced GO film can be suspended above the surface. FIG. 1 shows the boundary of one such suspended film. In this example, the reduced GO film is approximately 5 nm thick, and is electron transparent. Note that the Si pillars under the suspended film are clearly visible. The suspended film is mechanically stable when imaged with an atomic force microscope.

Figure 3:
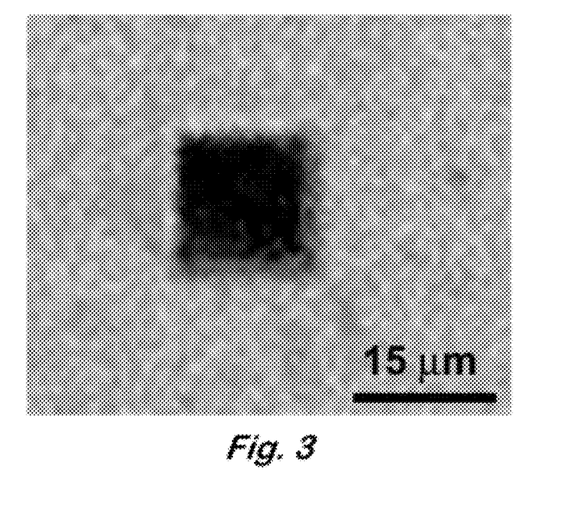
FIG. 3 shows an optical microscope image showing an isolated region of a suspended membrane. The black region is a suspended reduced GO film ~5 nm in thickness and the grey region is where the film is in contact with the surface.

In another embodiment, a suspended reduced GO thin-film is used as an electromechanical optical modulator. FIG. 3 shows an optical microscope image of a suspended, 5 nm thick film. Despite being only 5 nm thick, there is strong optical contrast between the suspended (black) and non-suspended (grey) regions in the figure. By electromechanically varying the separation of the suspended film and substrate, optical modulation is possible. The separation may be varied by a voltage source attached to the two electrodes in contact with the film. The voltage source applies a voltage that causes a portion of the suspended film to contact the substrate.

In another embodiment, a suspended reduced GO thin-film is used as a switch. The device is similar to the optical modulator, including a third electrode on the substrate below the suspended portion of the film. The voltage source can cause a portion of the suspended film to contact the third electrode to open or close the switch.

Another embodiment is the use of suspended reduced GO thin-films for nanofluidics. A reduced GO film can be locally suspended, forming long channels across a surface. The space between the suspended film and the contoured substrate forms the microfluidic channel. By tuning the initial film thickness and surface texturing, complex channel networks can be formed for nanofluidic applications. Moreover, the reduced GO film can be functionalized to allow for tunable fluid transport through the microchannels.

In another embodiment, the suspended film is part of a mass sensor. Particles that land on the suspended film can cause changes in its vibration. A laser interferometer may be used to measure these vibrations, which are then correlated to the mass of the particle. Alternatively, a capacitance meter can be used to measure a change in capacitance of the film caused by the particle.

In another embodiment, the suspended reduced GO membranes may be used as a filter for organic and biomolecular species or as a permeable membrane.

The technique to produce suspended reduced GO thin-films may have the following distinct advantages:
1) Low-cost production: The deposition and transferring of large-area reduced GO thin-films is possible using simple bench-top chemistry.
2) Versatile substrates: Because GO films can be deposited via spin-casting or air-brushing, they can be fabricated on a variety of substrates, as well as transferred to any substrate.
3) Selectivity: The chemistry of the release step for reduced GO thin-films is selective such that the film is only released from regions of the substrate that were in direct contact with the basic KOH or NaOH solution.

The following examples are given to illustrate specific applications. These specific examples are not intended to limit the scope of the disclosure in this application.

Example 1

Graphene Oxide Film Formation

Graphite oxide (GO) was formed via the Hummers method (Hummers et al., "Preparation of graphitic oxide" *J. Am. Chem. Soc.*, 80, 1339 (1958)) and then 1-5 mg of GO powder was suspended in 20 mL of $H_2O$ and ultrasonicated for at least 30 minutes. These solutions were then centrifuged at 10,000 rpms for 30 minutes and the resulting liquid and solids were separated. The still wet solid was suspended in nominally pure methanol and ultrasonicated for 30 minutes. This methanol solution was then centrifuged at 10,000 rpms for 15 minutes to remove residual unexfoliated solids.

A 200 µL micropipette was used to deposit the solution during spin-casting on $SiO_2$/Si samples, which typically measured 25×25 $mm^2$. The volume of individual droplets released on the spinning substrate was approximately 10 µL. Dry nitrogen was directed at the center of the spinning sample immediately after the GO solution spread across the surface. Film thickness was controllable on nanometer length scales by varying either the concentration of GO platelets in solution (typically between 0.5 mg/mL to 3.0 mg/mL) or the volume of solution (typically 50 µL to 500 µL). The thinnest continuous films are 1-4 monolayers thick and had a roughness of approximately 1 nanometer as confirmed by atomic force microscopy (AFM). A 10 nm thick film had a RMS roughness of approximately 2 nm.

Example 2

Reduced Graphene Oxide Film Transfer

After spin-casting, films were reduced in a hydrazine hydrate vapor for 20 hours on a hot plate set to 100° C. Subsequent to reduction, films were selectively delaminated from the $SiO_2$ substrate using a sodium hydroxide (NaOH) solution having a pH of 12.5. Single NaOH droplets (~10 µL) were slowly added to the rGO film surface and allowed to propagate across the sample. This process usually took several minutes. Next, the whole substrate, with the now delaminated rGO film and NaOH, was carefully submerged into a Petri dish filled with DI water. The delaminated rGO film floated on the top surface of the DI water. The floating film was subsequently recaptured by "scooping" it out with another substrate (usually pre-patterned $SiO_2$/Si). This somewhat aggressive technique can result in the film fracturing into smaller pieces on the order of several millimeters. Next, the film was allowed to dry in air.

Example 3

Suspended Films

To test the rGO elastic properties, rGO drum resonators were created by transferring films onto a pre-patterned, 250 nm $SiO_2$/Si substrate with holes etched through the oxide and ranging in diameter from 2.75 µm to 7.25 µm. In general, three final configurations were observed after film transfer: the film is pulled into the hole and contacts the bottom, the film spans the hole but ruptures presumably due to water escaping, or the film spans the hole intact but trapping water beneath it. In the present work, the trapped water was released by using a focused ion beam (FIB) to mill a small hole (<~300 nm) in the centers of the membranes.

Using a numerical solution (Leissa, Vibration of Plates (US Government Printing Office, Washington, D.C., 1969)) to an annular plate clamped on the outside, and free on the inside, it can be demonstrated that the small hole in the rGO film does not affect the fundamental frequency compared to the pristine resonator. The fundamental mode frequency parameters of a clamped circular plate and an annular plate clamped on the outside, and free on the inside with a hole in the center only begin to vary when the ratio of the hole radius, b, to the plate radius, a, is larger than 0.2. Even at b/a=0.3, the fundamental frequency is only 11.5% higher. Here the b/a ratio was typically no larger than 0.1, which corresponds to a fundamental frequency shift due to the hole of approximately 0.3%. In addition, numerical models using Ansys, a simulation software package, also showed very little change in fundamental frequency with or without the FIB induced hole.

Example 4

Interferometric Measurements

Figure 4:
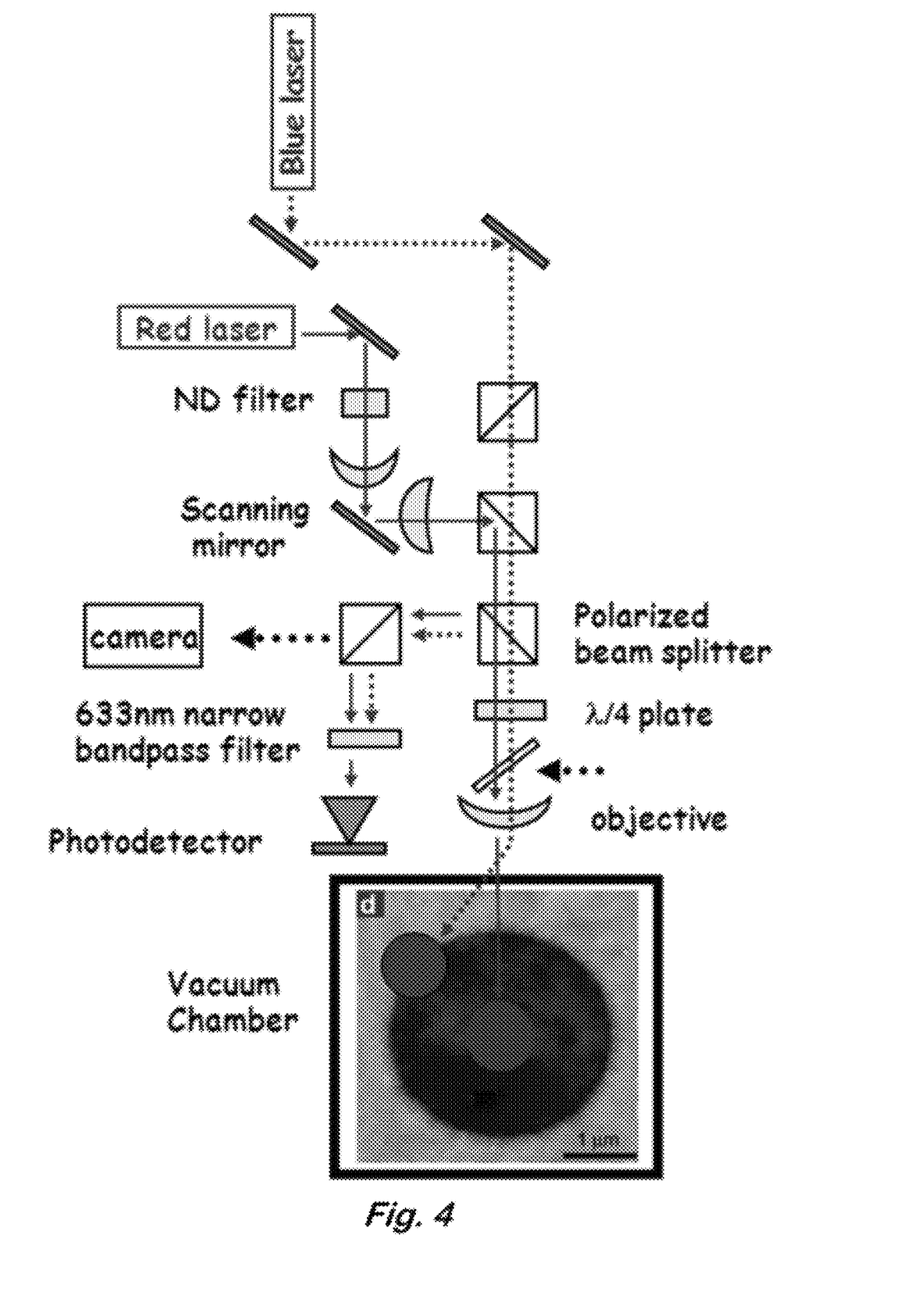
FIG. 4 is a schematic showing the interferometry setup used for resonance measurements. Both the red and blue laser spots are approximately 1 μm in diameter.

Optical transduction was used to study the vibratory response of the suspended rGO membranes. A schematic of the optical setup is shown in FIG. 4. A long working distance, glass corrected, objective lens was used to focus two laser beams each into approximately 1 micron diameter spots on the sample located in a vacuum chamber ($<10^{-7}$ Torr). The optical path of one of the lasers (blue, wavelength 412 nm) was fixed and its focused spot was positioned using a motorized linear stage, which moves the entire vacuum chamber. The other laser beam (red HeNe 633 nm) was equipped with motorized steering mirrors, which allowed independent positioning of the red focus within the 60×60 μm² image area provided by a CCD camera. A point-type thermoelastic excitation was provided by modulating the intensity of the blue diode laser (412 nm) focused on a single suspended rGO membrane. The amplitude of the laser power modulation delivered to the sample was less than 50 μW. The time-variable local heating induced by the focused, modulated blue laser beam generates a modulated stress due to thermal expansion and thus provided the driving force to excite the membranes into resonance. The resulting motion of the suspended structures was detected interferometrically, by focusing another laser (red CW HeNe, 633 nm) on the membrane and measuring the modulation of the reflectivity using a spectrum analyzer and a photodetector with a 633 nm bandpass filter. This modulation originates from the motion-induced variation of the gap in a Fabry-Perot interferometer created by the rGO membrane (acting as a semitransparent mirror) and the underlying substrate.

Example 5

Tension in rGO Membranes

Figure 5:
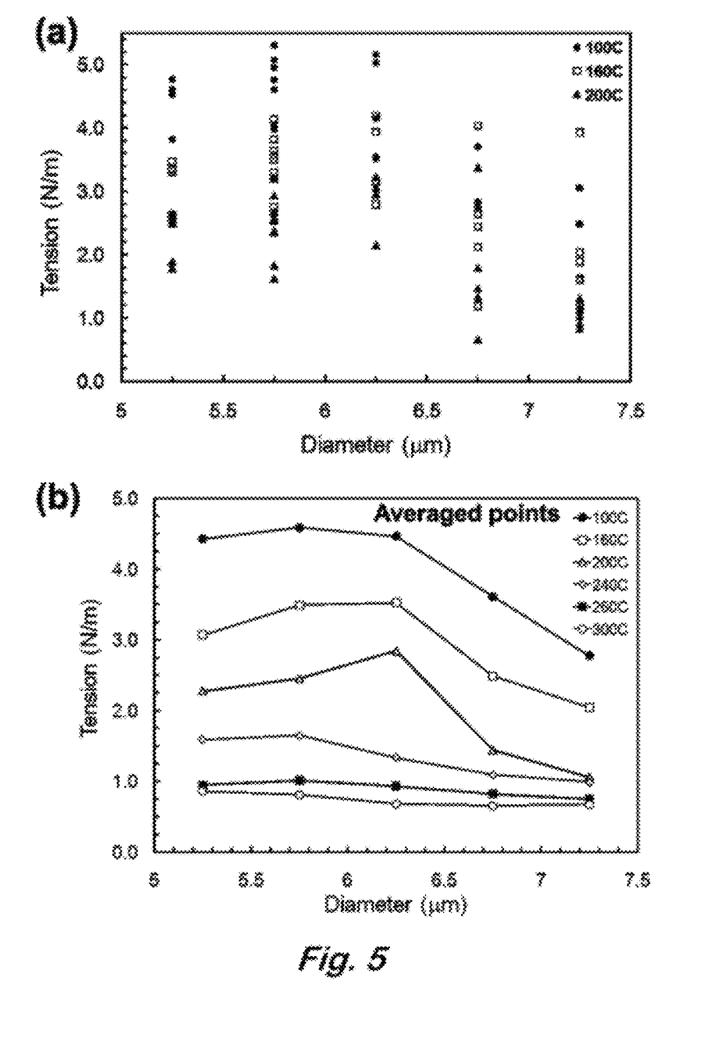
FIG. 5 shows plots of tension vs. resonator diameter.

Since the as-fabricated rGO drums are under tension, the following equation can be used to extract the magnitude of this tension from the frequency response:

$$f_{mn} = \frac{1}{2a}\sqrt{\frac{T}{\rho h}}\beta_{mn}$$

where h is the film thickness, a is the drum radius, $\rho$ is the material density, T is tension, and $\beta_{nm}$ is the $n^{th}$ root of the $m^{th}$-order Bessel function. FIG. 5(a) shows the calculated tension for multiple resonators after annealing at 100, 160, and 200° C. For each of these annealing temperatures the rGO membranes were flat and under tension and can be adequately described by the membrane model from the above equation. The tension was released during annealing at subsequently higher temperatures. Extracting tension values for all annealing temperatures shows the average tension release significantly slows after the 240° C. anneal (FIG. 5(b)). At this point it can no longer be assumed the rGO drums follow the membrane model.

Figure 6:
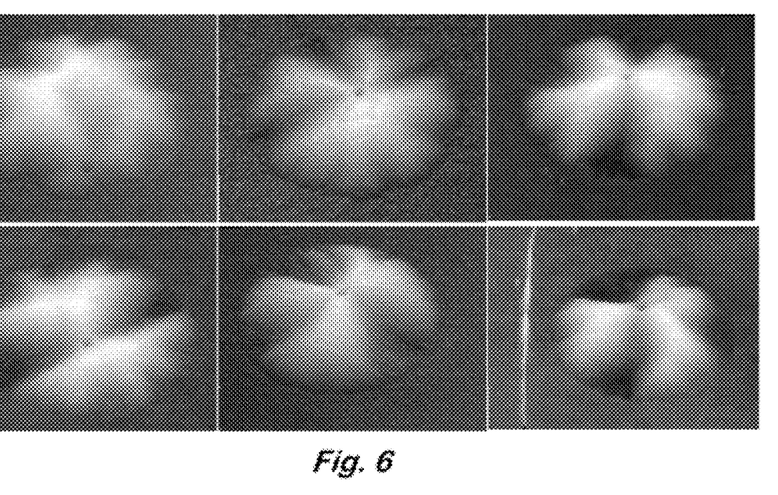
FIG. 6 shows perspective AFM height images showing six different resonators which have formed a dome-like shape during the annealing process.

The release of built-in tension for these rGO resonators results in a physical deformation of the suspended structures. Most rGO resonators form corrugations around 240° C. to 260° C., and all have corrugations by 300° C. FIG. 6 shows representative AFM images of six different membranes after the 300° C. anneal. The dome-like shapes, in addition to the fact that these structures did not noticeably change between the 260° C. and 300° C. anneal, indicate they are in the limit of zero tension. The maximum vertical distance measured for all corrugated structures was 170 nm above the flat surface and corresponds to a aspect ratio of ~1:43 (height: diameter). Thus, significant "thinning" of the material during deformation is not expected.

Example 6

Interferometry Results

Figure 7:
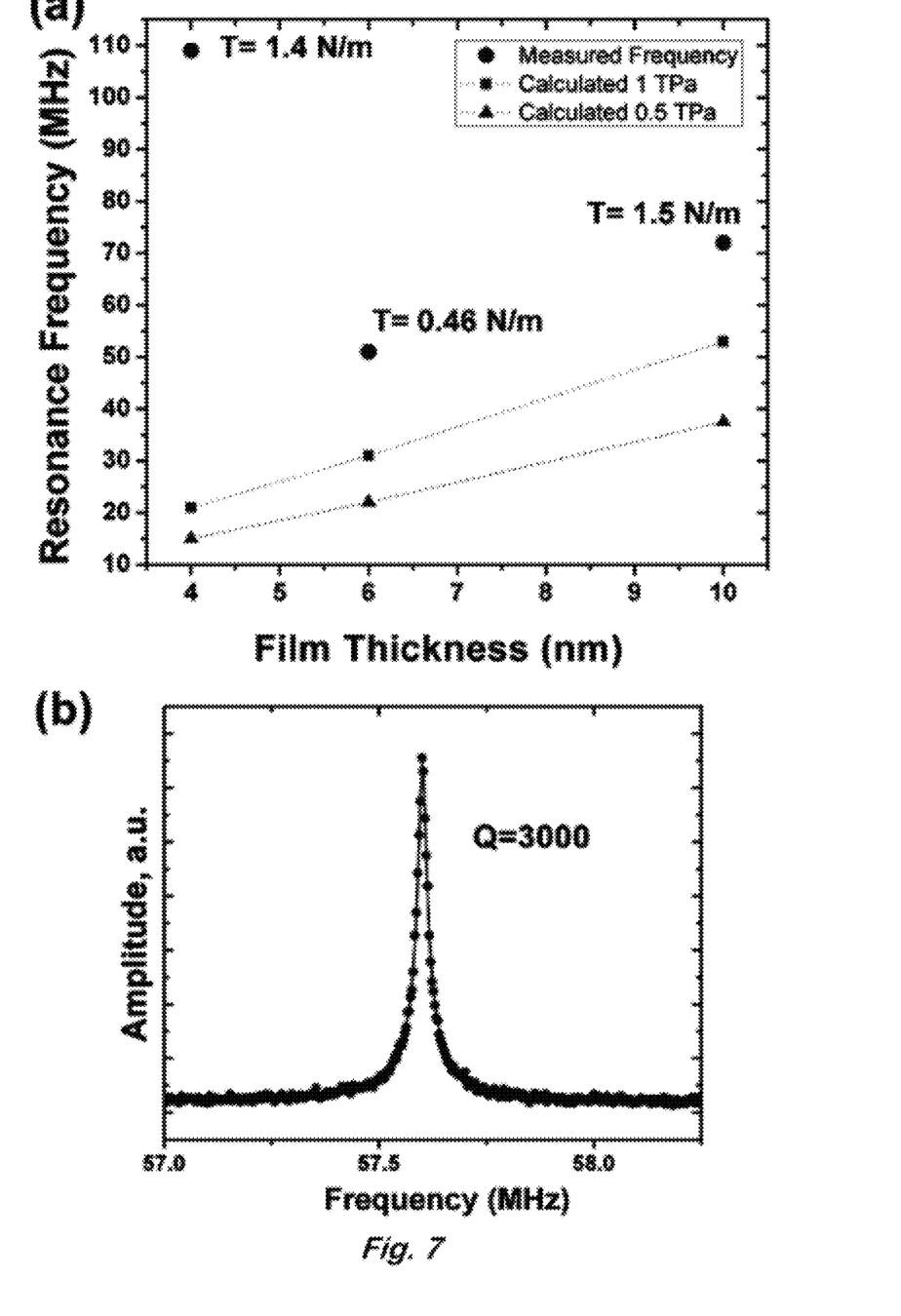
FIG. 7 shows the frequency response of reduced graphene oxide (rGO) resonators. (a) The fundamental resonance frequency versus film thickness for rGO drum resonators (diameter=2.75 μm). The theoretical values for a flat circular plate with E=1 TPa (squares) and 0.5 TPa (triangle) are also shown. Assuming membrane behavior, the tension (T) for each resonator is calculated. (b) Frequency versus amplitude for the 6 nm thick drum resonator shown in (a) demonstrating a Q-value of 3000.

Laser interferometry was used to probe the elastic properties of the suspended rGO drum resonators (Bunch et al., "Electromechanical Resonators from Graphene Sheets" *Science*, 315, 490-493 (2007); Bak et al., "High-frequency micromechanical resonators from aluminium-carbon nanotube nanolaminates" *Nat. Mater.*, 7, 459-463 (2008)). The mode spacings of the resonance frequencies depend on the tension (T) in the drum which can act either as a plate (T≈0) or as a membrane (T>0). Determination of Young's modulus (E) is straightforward when the drum vibrates in the plate mode. For a circular plate the frequency modes are given by $$f_{mn} = \frac{\pi h}{4a^2}\sqrt{\frac{E}{3\rho(1-s^2)}}(\beta_{mn})^2$$

where h is the film thickness, a is the drum radius, $\rho$ is the material density, s is Poisson's ratio, and $\beta_{nm}$ is the $n^{th}$ root of the $m^{th}$-order Bessel function. When under tension the circular drum frequencies follow a membrane behavior given by the formula in Example 5. FIG. 7(a) shows the measured values for the fundamental resonance frequency of a 4, 6, and 10 nm thick rGO membrane. For all thicknesses $f_o$ is significantly higher than the calculated fundamental mode of a relaxed plate, assuming a Young's modulus as found in graphene (E=0.5 TPa (Frank et al., 2558-2561 (AVS, 2007)) or 1 TPa (Bunch et al., "Electromechanical Resonators from Graphene Sheets" *Science*, 315, 490-493 (2007)), suggesting that the drums are under tension (FIG. 7(a)). Built-in tension has been observed for graphene resonators and often results from the fabrication process. Fortuitously, this built-in tension together with enhanced adhesion to the $SiO_2$ substrate from remnant oxygen groups significantly improves quality factors (Q) over pure graphene resonators. Graphene resonators typically have Q-values of 10 to 200, whereas the present rGO resonators consistently show quality factors over 1500 (FIG. 7(b)) with 4000 the highest value measured to date. These values compare favorably with state-of-the-art diamond resonators which typically have Q-values of ~3000 at room temperature.

Figure 8:
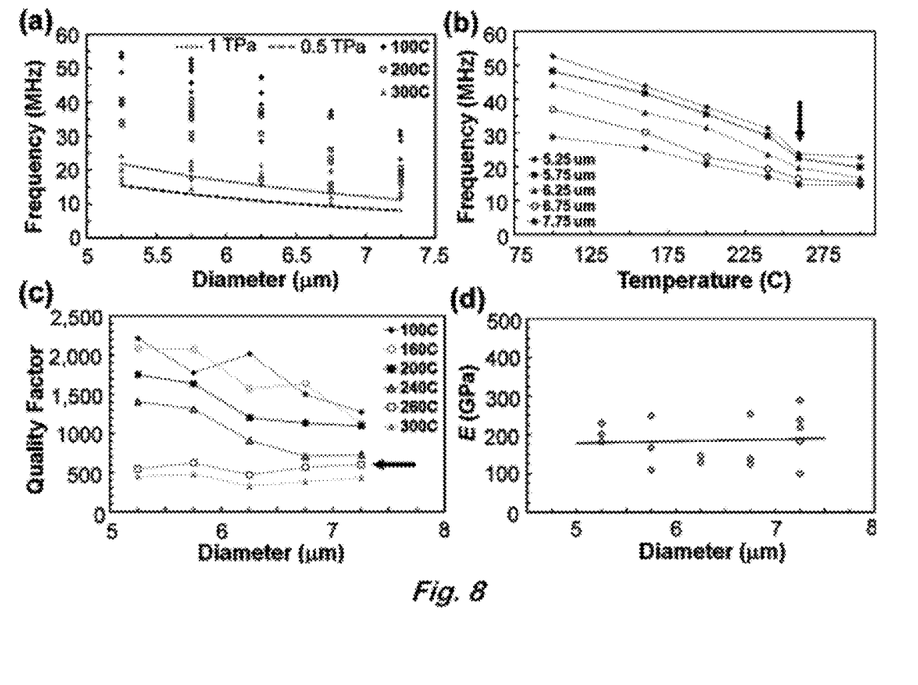
FIG. 8 shows stress relaxation and Young's modulus of rGO. (a) The fundamental resonance frequency ($f_o$) versus drum diameter (D) for a series of rGO drums after thermal annealing. (b) Average $f_o$ versus temperature for differently sized resonators. The arrow highlights when the membranes predominantly form wrinkles (c) The average quality factor (Q) vs. drum diameter. After wrinkle formation at ~260° C. the Q-values are relatively constant across all diameters. (d) Extracted Young's modulus from FEM calculations versus hole diameter.

Extracting the Young's modulus requires removal of the tension in the film which was accomplished through thermal annealing. FIGS. 8(a) and (b) shows $f_o$ verses drum diameter for a 15 nm thick film after annealing in argon at different temperatures for at least one hour. As described below after annealing at 300° C. the membranes are in the limit of zero tension. When membranes are annealed at successively higher temperatures $f_o$ monotonically decreases as tension is released (FIGS. 8(a) and (b)), with the highest starting value calculated at 5.3 N/m. Note that annealing not only results in a drop of $f_o$ but also a narrowing of the frequency distribution as resonators converge to zero tension.

Annealing between approximately 240° C. and 260° C. causes the originally flat membranes begin to wrinkle resulting in a transition in both the $f_o$ vs. temperature (FIG. 8(b)) and Q vs. temperature (FIG. 8(c)) curves. The wrinkling of the film strongly indicates that film relaxation does not primarily occur through uniform platelet slipping since this would result in a smooth film. Rather, it appears that either localized regions of the membrane surface slip causing non-uniform tension and buckling, or that the film slips as a whole potentially due to film adhesion being compromised at the drum rim. This latter interpretation is supported by the observation that the Q-values decreased during annealing, then remain constant after wrinkle formation around 260° C. The maximum ratio for out-of-plane deformation to drum diameter is ~1:45 (or 2%).

After annealing at 300° C. the suspended membranes were sufficiently relaxed to allow extraction of Young's modulus from the frequency response. FIG. 8(a) shows frequency data for a series of the same resonators after annealing along with the theoretical calculations for a flat circular plate with E=0.25, 0.5, and 1 TPa. The final wrinkled state causes $f_o$ to deviate enough from the flat plate approximation such that finite element modeling (FEM) is necessary to more accurately extract E. FIG. 8(d) shows the FEM results after modeling 19 textured drums and shows the modulus averages 175 GPa with a standard deviation of 60 GPa. This value is close to that recently reported for single, isolated GO sheets reduced via hydrogen plasma treatment and is several times higher than that found in macroscopic GO paper.

This high Young's modulus for rGO films raises questions regarding the balance between the intra-platelet stiffness and inter-platelet shear forces. The average lateral dimensions of a single GO platelet measure approximately 1 μm, which means multiple overlapping sheets are necessary to span the 2.75 μm to 7.25 μm gaps. Even so, the frequency response demonstrates the Young's modulus is primarily dictated by the intra-platelet elastic response as opposed to the presumably weaker platelet-platelet interactions. It has been predicted that even a small addition of oxygen will significantly stiffen graphene sheets (Incze et al., "Mechanical properties of graphite oxides: Ab initio simulations and continuum theory" Phys. Rev. B, 70, 212103 (2004)), which is likely playing a role in the high mechanical rigidity.

Example 7

Sensors

Figure 9:
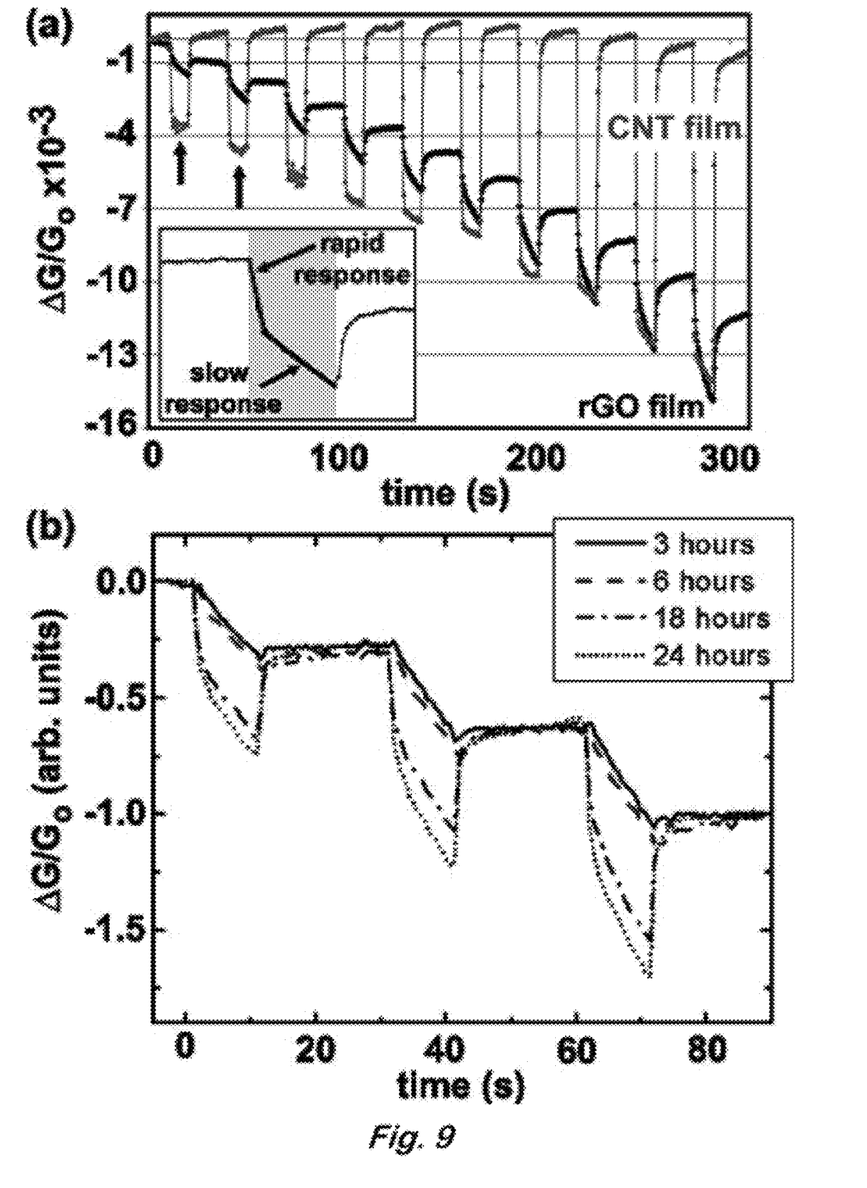
FIG. 9 shows (a) real-time conductance response to 5 s acetone pulses of increasing concentration for a SWNT network sensor (upper curve) and a rGO network sensor (lower curve). Arrows on the plot mark the first two of ten pulses, which increase in concentration from $P/P_o$) 0.025% to $P/P_o$) 1%, where $P_o$ is the vapor pressure of acetone. Inset: close-up of the fifth pulse highlighting the "rapid" and "slow" response of the rGO device. (b) Plot of the normalized conductance response to 5 s pulses of acetone for GO devices reduced with hydrazine for 3, 6, 18, and 24 h. With increasing reduction time the fast response increases while the slow response decreases.

Before additional processing the GO films were heated in argon to 150° C. for 15 min to remove residual solvent and water. Standard photolithography was then used to create interdigitated arrays of Ti/Au electrodes with finger spacings ranging between 10 and 340 μm. Processed samples were subsequently reduced back toward graphene by exposure to a hydrazine hydrate vapor up to 24 h while being heated to 100° C. To test the sensor response of these reduced graphene oxide devices they were exposed them to 5 s pulses of dilute acetone vapor in air while simultaneously measuring the relative change in electrical conductance (ΔG/Go). The response observed for acetone is typical of most of the vapors tested. FIG. 9(a) shows a comparison of the real-time conductance response of a GO device reduced for 17 h in hydrazine vapor to the conductance response of a SWNT network device of similar total area to increasing concentrations of acetone vapor. Analysis of the curves in FIG. 9(a) can be broken into two parts: the "rapid" (steep slope) and "slow" (shallow slope) response. The rapid response arises from molecular adsorption onto low-energy binding sites, such as $sp^2$-bonded carbon, and the slow response arises from molecular interactions with higher energy binding sites, such as vacancies, structural defects, and oxygen functional groups. Adsorption on $sp^2$-bonded carbon occurs through weak dispersive forces, while at a defect such as a carboxylic acid group single- and double hydrogen bonding allows binding energies of at least several hundred meV/molecule. As is evident from FIG. 9(a), the rapid response is recoverable, whereas the slow response is generally nonrecoverable without moderate heating, and leads to integration of the conductance signal.

The striking difference between the rapid and slow response of the SWNT and rGO device may be because the intrinsic concentration of oxygen defects on SWNTs is quite low. On the other hand, the almost one-to-one ratio between the rapid and slow response of the rGO devices is a direct reflection of the remnant high-energy adsorption sites after incomplete reduction. Because oxygen defects can play a dominant role in the sensor characteristics of SWNTs, oxygen defect density is expected to heavily influence the conductance response of the rGO material as well. To systematically study this, GO devices were exposed to hydrazine hydrate vapor for different times, thereby changing the oxygen defect density. FIG. 9(b) shows normalized responses to acetone for GO devices reduced at different intervals. A clear trend is observed in the response, with increasing reduction time the rapid response increases and the slow response decreases. This is consistent with the fact that the number of $sp^2$-bonded carbon sites increases while at the same time the higher-energy adsorption sites (i.e., oxygen functional groups) decrease.

To date, the temporal evolution of GO chemistry during hydrazine reduction remains vague. After long exposures the oxygen to carbon ratio is reduced from approximately 1:3 to 1:10. In these samples it has also been found that ~25% of the rGO carbons remain functionalized (Stankovich et al., J. Mater. Chem., 16(2), 155-158 (2006). Reaction mechanisms (Stankovich et al., Carbon, 45(7), 1558-1565 (2007)) and FT-IR measurements (Li et al., Nat. Nano., 3(2), 101-105 (2008)) suggest carboxyl groups make up the largest portion of these unreduced groups, though epoxides and alcohols are undoubtedly present as well. From the data shown in FIG. 9(b) only general statements can be made about surface chemistry due to the range in remnant oxygen functional group types, as well as density. It is clear, however, that hydrazine reduction is a knob with which to tune the sensing response of GO-based devices.

When chemical sensor performance is considered, there are two important parameters. As discussed above, one of these parameters is the sensitivity of the conductance response to molecular adsorbates. The second significant consideration is the low-frequency noise, which is generally dominated by 1/f noise. The 1/f noise arises from fluctuations in carrier mobility (Ishigami et al., Appl. Phys. Lett., 88(20), 203116-3 (2006)) or carrier density (Lin et al., Nano Lett., 6(5), 930-936 (2006)) and is ubiquitous in solid-state devices (Hooge, IEEE Trans. Electron Devices, 41, 1926 (1994)). In the case of SWNTs such fluctuations can arise from trapped charges in the oxide or the presence of defects within individual tubes. It was recently shown (Lin et al., Nano Lett., 8(8), 2119-2125 (2008)) that 1/f noise in bilayer graphene is strongly suppressed compared to nanotubes even in the presence of similar oxides. An effective screening of charge fluctuations from external impurity charges is identified as the root of this difference.

Such screening could explain the 10-100 fold reduction in 1/f noise in rGO sensors over SWNT-based sensors, as shown in FIG. 10. This figure compares the low frequency noise density spectrum of a SWNT device and two rGO devices and reveals that the noise level in rGO devices strongly decreases with increasing film thickness. The shaded region of FIG. 10 shows the noise variation as film thickness is varied from an average of 2 to 4 nm. Films over 4 nm consistently show noise response at the thermal noise limit of the experimental setup. The increase in charge carrier number from a 2 nm to a 4 nm film would not be expected to decrease the noise 10-fold and suggests that impurity charge screening is further reducing 1/f noise. FIG. 11 demonstrates the important role of noise reduction by comparing the responses of SWNT and rGO devices to 0.5 ppb 2,4-dinitrotoluene (DNT), a simulant for the explosive TNT. The lower noise levels in the rGO device lead to a notable increase in signal-to-noise ratio.

Figure 12:
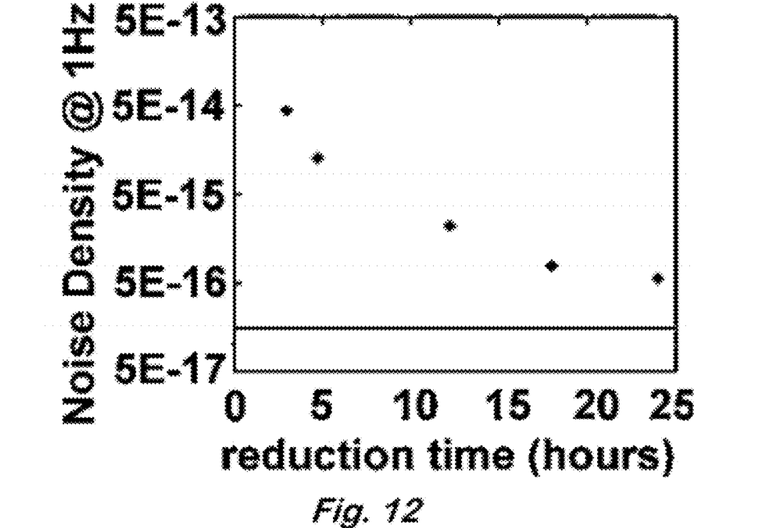
FIG. 12 shows a plot of noise density at 1 Hz vs. hydrazine reduction time for GO films with the same thickness. The line marks the thermal noise limit.

The extent of chemical reduction also affects low frequency noise. Films exposed to hydrazine vapor for longer times show reduced 1/f noise, as revealed in FIG. 12. (Note that this trend is also observed for the curves shown in FIG. 11). As the GO material is reduced back toward graphene there is a large increase in film conductivity. In turn this leads to a reduction in noise levels of rGO devices.

The benchmark for chemical sensors is the minimal detectable level (MDL), which comprises both the sensor response due to adsorption and the device noise level. For SWNT sensors the lowest MDLs are realized in a capacitance-based measurement mode (Snow et al., Chem. Soc. Rev., 35, 790-798 (2006)) due to reduced 1/f noise. Therefore, the SWNT capacitance response MDLs was used as a basis of comparison here. Table 1 compares the MDLs achieved for capacitance-based SWNT sensors (Snow et al., Nano Lett., 5(12), 2414-2417 (2005)) and conductance-based rGO sensors to 10 s exposures (ten seconds is the fastest target response time set by The Joint Chemical Agent Detector (JCAD) program) to simulants of an explosive and the three main classes of chemical warfare agents—blood, blister, and nerve agents. In addition, the target specifications of a portable detector for military applications, called The Joint Chemical Agent Detector (JCAD) (Laljer, Joint Chemical Agent Detector (JCAD): The Future of Chemical Agent Detection, 11th Annual US Army Ground Vehicle Survivability Symposium, Mar. 27-30, 2000), are also compared, as well as exposure limits set by the Center for Disease Control (CDC) (Center for Disease Control and Prevention. http://www.bt.cdc.gov/agent/, 2008).

TABLE 1

Comparison of the MDLs for a SWNT network sensor and a rGO network sensor

| Simulant | SWNT: 10 s (ppb) | rGO: 10 s (ppb) | JCAD specifications ≤10 s (ppb) | CDC specifications (ppb) |
|---|---|---|---|---|
| HCN | >4000 | 70 | $2 \times 10^6$ | $5 \times 10^4$ |
| CEES | 0.5 | 0.5 | 7500 | 0.5 |
| DMMP | 0.1 | 5 | 170 | 17 |
| DNT | 0.1 | 0.1 | — | — |

Figure 13:
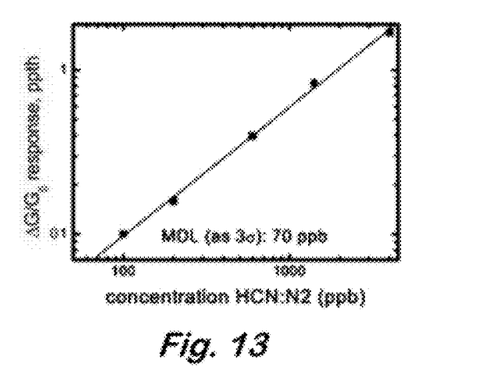
FIG. 13 shows the response of a rGO sensor to decreasing levels of hydrogen cyanide (HCN).

FIG. 13 shows the normalized response $\Delta G/G_o$ of an rGO device to 10 s doses of increasing concentration of hydrogen cyanide (HCN) in nitrogen. The MDL is defined here as that concentration of vapor which gives rise to a change in conductance $\Delta G$ that is exactly three standard deviations from $G_o$ (i.e., a signal-to-noise ratio of three). Assuming a linear response function, it was found that the MDL is 70 ppb. For SWNTs HCN was not detected at the highest concentration tested (4000 ppb). For other simulants such as chloroethyl-ethyl sulfide (CEES, a simulant for sulfur mustard gas) is and DNT comparable MDLs were found between rGO conductance-based and SWNT capacitance-based detection, whereas the MDL for dimethylmethylphosphonate (DMMP, a simulant for sarin) is an order of magnitude lower for SWNT sensors (Table 1). These results highlight how different classes of molecules can distinctly interact with different surface sites. HCN weakly interacts with nominally pristine $sp^2$-bonded nanotubes while strongly interacting with remnant defects in rGO; the reverse is true for organophosphates (i.e., DMMP), and the responses to aromatics and alkane derivatives are similar (i.e., DNT and CEES, respectively). Thus, these two carbon-based nanomaterials can provide complimentary capabilities of chemical agent detection and further stress the importance of tailoring surface chemistry to enhance sensitivity.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A method comprising:
   centrifuging a suspension of graphene oxide platelets and water to form a liquid and wet solids;
   removing the wet solids from the liquid;
   suspending the wet solids in an organic solvent to form a mixture;
   spin coating the mixture by placing a drop of the mixture on a spinning substrate while blowing a drying gas onto the substrate and allowing the water and the organic solvent on the substrate to evaporate; and
   repeating the spin coating one or more times to form a graphene oxide film in contact with the substrate.

2. The method of claim 1, wherein the organic solvent is methanol.

3. The method of claim 1, wherein each spin coating produces a sub-monolayer of graphene oxide on the substrate.

4. The method of claim 1, wherein the spin coating is repeated up to 300 times.

5. The method of claim 1, wherein the substrate is spun from about 2000 to about 6000 RPM.

6. The method of claim 1, wherein the drop of the mixture is up to about 100 µL in volume.

7. The method of claim 1, further comprising:
   at least partially reducing the graphene oxide film.

8. The method of claim 7, wherein the graphene oxide film is reduced with hydrazine hydrate vapor.

9. The method of claim 7, wherein the graphene oxide film is reduced by annealing in an inert gas or hydrogen.

10. The method of claim 7, further comprising;
    releasing the reduced graphene oxide film from the substrate; and
    placing the released film on a second substrate.

11. The method of claim 10, wherein the reduced graphene oxide film is released with a sodium hydroxide solution or potassium hydroxide solution.

12. A method comprising:
    providing a mixture of graphene oxide platelets, water, and an organic solvent;
    spin coating the mixture by placing a drop of the mixture on a spinning substrate while blowing a drying gas onto the substrate and allowing the water and the organic solvent on the substrate to evaporate; and
    repeating the spin coating one or more times to form a graphene oxide film in contact with the substrate;

at least partially reducing the graphene oxide film;

releasing the reduced graphene oxide film from the substrate; and placing the released film on a second contoured substrate such that portions of the film are suspended above the contoured substrate.

13. The method of claim 12, wherein the organic solvent is methanol.

14. The method of claim 12, wherein each spin coating produces a sub-monolayer of graphene oxide on the substrate.

15. The method of claim 12, wherein the spin coating is repeated up to 300 times.

16. The method of claim 12, wherein the substrate is spun from about 2000 to about 6000 RPM.

17. The method of claim 12, wherein the drop of the mixture is up to about 100 μL in volume.

18. The method of claim 12, wherein the graphene oxide film is reduced with hydrazine hydrate vapor.

19. The method of claim 12, wherein the graphene oxide film is reduced by annealing in an inert gas or hydrogen.

20. The method of claim 12, wherein the reduced graphene oxide film is released with a sodium hydroxide solution or potassium hydroxide solution.

* * * * *